United States Patent
Deák et al.

[11] 3,946,018
[45] Mar. 23, 1976

[54] 1,4-DIHYDRO-3 (2H)-ISOQUINOLINONE DERIVATIVES

[75] Inventors: Gyula Deák; Margit Dóda; Lajos György; László Hazai, all of Budapest, Hungary; Klára Pfeifer, deceased, late of Budapest, Hungary, by György Mihaly, residuary legatee

[73] Assignee: Egyt Gyogyszervegyeszeti Gyar, Budapest, Hungary

[22] Filed: Feb. 5, 1974

[21] Appl. No.: 439,823

[30] Foreign Application Priority Data
Feb. 12, 1973 Hungary............................ EE 2093
Nov. 13, 1973 Hungary............................ EE 2093

[52] U.S. Cl............................. 260/287 D; 424/258
[51] Int. Cl.²........................................ C07D 217/24
[58] Field of Search...... 260/287 D, 287 K, 287 CE, 260/287 R

[56] References Cited
FOREIGN PATENTS OR APPLICATIONS
162,784   11/1974   Hungary OTHER PUBLICATIONS
Morimoto, "J. Pharm. Soc. Japan" 62, 446–452 (1952).

Primary Examiner—R. Gallagher
Assistant Examiner—David E. Wheeler
Attorney, Agent, or Firm—Young & Thompson

[57] ABSTRACT

Compounds of the formula

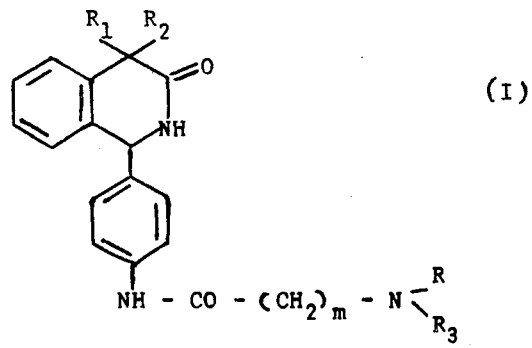

(I)

wherein
 $R_1$ and $R_2$ each represent hydrogen or a straight-chained or branched $C_{1-3}$ alkyl group,
 R stands for hydrogen or a straight-chained or branched $C_{1-4}$ alkyl group,
 $R_3$ stands for hydrogen or a straight-chained or branched $C_{1-4}$ alkyl group.

The new compounds of formula (I) possess valuable pharmacological properties, and act, primarily, on the central nervous system. Thus they can be used in the therapy first of all as the active agents of anticonvulsive medicines.

3 Claims, No Drawings

1,4-DIHYDRO-3 (2H)-ISOQUINOLINONE DERIVATIVES

This invention relates to novel 1,4-dihydro-3(2H)-isoquinolinone derivatives.

The new compounds according to the invention correspond to the formula wherein

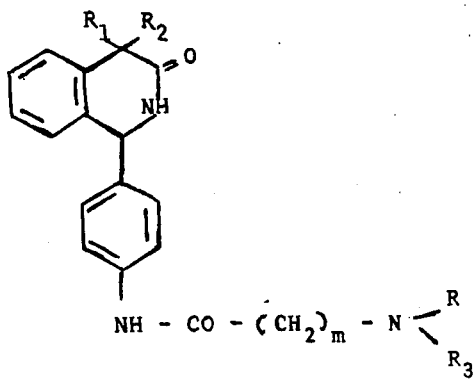

(I)

wherein
$R_1$ and $R_2$ each represent hydrogen or a straight-chained or branched $C_{1-3}$ alkyl group,
R stands for hydrogen or a straight-chained or branched $C_{1-4}$ alkyl group,
$R_3$ stands for hydrogen or a straight-chained or branched $C_{1-4}$ alkyl group, and
R and $R_3$ may form together with the adjacent nitrogen atom.

The compounds of formula (I) are of basic character, and form acid addition salts. These salts are also covered by the scope of the invention.

The new compounds of formula (I) possess valuable pharmacological properties, and act, primarily, on the central nervous system. These compounds block the spasm provoked by electric current or by pentamethylenetetrazole. On the basis of their pharmacological properties, the compounds of the general formula (I) can be used in the therapy primarily as the active agents of anticonvulsive medicines.

The pharmacological properties of the new compounds were tested on white mice of both sexes, weighing 16 to 24 g. The new compounds were administered orally through a metal stomach tube, in the form of a 5 per cent suspension in a medium containing Tween 80 as suspending agent.

The $LD_{50}$ values of the compounds were determined on groups each consisting of 8 mice. The results were evaluated according to the method of Lichtfield and Wilcoxon (J. Pharmacol. exp. Therap. 96, 99 [1949]).

The paralyzing effect of the compounds was tested on groups each consisting of 8 mice, by the rotarod test. The $ED_{50}$ rotarod value corresponds to the dosis, which, one hour after the administration, causes 50 per cent of the test animals to fall down from the rotarod within 3 minutes. The neurotoxic activity was evaluated according to the method of Lichtfield and Wilcoxon.

The electroshock-inhibiting effect of the compounds was examined on groups each consisting of 10, individually caged mice. The anticonvulsive activity was tested by the "Maximum Electroshock Seizure Test" of Swinyard, et al. (Epilepsia 10, 107 [1969]), and the inhibition of the tonic extension of the hind limbs was evaluated. The $ED_{50}$ ES value corresponds to the dosis which, 1 hour after the administration, has a protecting effect for 50 % of the animals. The results were evaluated according to the method of Lichtfield and Wilcoxon. The electroshock was provoked using corneal electrodes, under the following parameters: 50 Hz, 0.3 sec. 3 msec; the current intensity varied between 28 and 34 mA (a current intensity was maintained that was sufficient to provoke spasm in each of the 10 animals).

The activities of the compounds with protecting effect against electroshock were compared by the so-called protective index, which was calculated by dividing the individual $ED_{50}$ rotarod values with the corresponding $ED_{50}$ ES values. The greater this ratio, the more remote the dosis protecting against electroshock is from the dosis causing muscle relaxation.

The inhibiting effect on pentamethylenetetrazole-provoked spasm was tested on groups each consisting of 12 individually caged, randomized mice, by the method of Orloff (Proc. Soc. Exp. Biol. Med. N.Y., 70, 254 [1949]). The pentamethylenetetrazole spasm threshold was determined by the slow (0.05 ml./10 sec.) intravenous administration of a 0.5 % pentamethylenetetrazole solution, and the influence of the compounds on the spasm threshold was examined. In every case, the tonic extension of the hind limbs was regarded as spasm.

The results of these tests are listed in Table 1. For comparison various known and widely used pharmacons, namely phenobarbital (5-ethyl-5-phenylbarbituric acid), phenytoin (5,5-diphenylhydantoine) and trimethadion (3,5,5-trimethyl-2,4-oxazolidine-dione) were also tested under the same conditions. The results are also given in the Table.

The data listed in the Table show that the compounds of the invention are of low toxicity, and most of them have a protective index 1 to 2 orders of magnitude greater than the known reference substances.

Table 1

| Compound (Example No.) | $LD_{50}$ mg./kg. | $ED_{50}$ rotarod 3 h.,mg./kg. | $ED_{50}$ ES 3 h., mg./kg. | Protective Index | $ED_{50}$ pentamethylenetetrazole 3 h., mg./kg. |
|---|---|---|---|---|---|
| 5 | cca 2000 | 490 | 21 | 24 | 50 |
| 6 | 1600 | 435 | 32 | 13.6 | 100 |
| 7 | >1600 | 340 | 22 | 15.4 | 50 |
| 8 | 600 to 800 | cca 50 | cca 20 | cca 2.5 | 50 |
| 9 | >1600 | 520 | 10.2 | 51 | 50 |
| 10 | >2000 | 760 | >300 | cca 2 | 50 |
| 11 | cca 600 | 270 | 22 | cca 12 | 50 |
| 12 | >1000 | 270 | 10.5 (54.0 – 110.0) | 26 | 100 |
| 13 | >2000 | cca 800 | 25 | cca 32 | — |
| 14 | >2000 | cca 1600 | 27.0 (20.8 – 35.2) | cca 59 | — |

Table 1-continued

| Compound (Example No.) | LD$_{50}$ mg./kg. | ED$_{50}$ rotarod 3 h.,mg./kg. | ED$_{50}$ ES 3 h., mg./kg. | Protective Index | ED$_{50}$ pentamethylenetetrazole 3 h., mg./kg. |
|---|---|---|---|---|---|
| 15 | >1000 | cca 300 | 29 | cca 10 | — |
| 16 | cca 1600 | cca 1300 | cca 88 | cca 15 | — |
| 30 | >1000 | cca 400 | cca 50 | cca 8 | — |
| 5-ethyl-5-phenyl-barbituric acid | 180 | 38 | 15 | 2.5 | 15 |
| 5,5-diphenyl-hidantoine | 300 | 10 | 10 | 1.0 | 25 |
| 3,5,5-trimethyl-2,4-oxazolidine-dione | 1750 | 340 | 440 | 0.77 | 62 |

The compounds of formula (I) are prepared as follows:

A 1-(4'-aminophenyl)-1,4-dihydro-3(2H)-isoquinolinone derivative of the formula

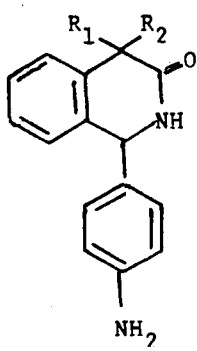

(II)

wherein $R_1$ and $R_2$ each have the same meanings as defined above, is reacted with a carboxylic acid derivative of the formula

A — (CH$_2$)$_m$ — COR$_4$    (III)

wherein m is one, $R_4$ stands for halogen or ethoxycarbonyloxy, and A stands for halogen or benzyloxycarbonylamino, to form a compound of the general formula (IV),

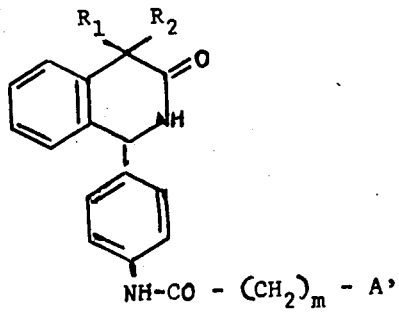

(IV)

wherein $R_1$ and $R_2$ each have the same meanings as defined above, and m is one, and A' stands for halogen or benzyloxycarbonylamino, and the compound of formula (IV), wherein A' stands for ethoxy or halogen, is reacted with an amine of the formula

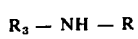

$R_3$ — NH — R    (V)

wherein R and $R_3$ each have the same meanings as defined above, or the compound of formula (IV), wherein A' stands for benzyloxycarbonylamino, is subjected to catalytic hydrogenation.

The compounds of formula (I) can be converted into their acid addition salts by reacting them with a pharmaceutically acceptable organic or mineral acid.

The compounds of formula (II), used as starting substances in the process of the invention, can be prepared as described in Hungarian Patent Specification No. 162,784. The starting compounds of formula (III) are known, mostly commercially available substance.

The acylamine intermediates of formula (IV) are new substances.

According to a preferred method a compound of formula (II) is reacted with a ω-chlorocarboxylic chloride of formula (III), wherein A and $R_4$ each stand for chlorine, and the obtained acylamine of formula (IV), wherein A' stands for chlorine and m is one, is reacted with an amine of formula (V). This method leads to compounds of formula (I), wherein R and/or $R_3$ represent a group other than hydrogen, and m is one.

According to a further preferred method a starting compound of formula (II) is reacted with an N-(benzyloxycarbonyl)-ω-aminoacid chloride of the general formula (III), wherein $R_4$ stands for chlorine and A represents a benzyloxycarbonylamino group, or with a mixed anhydride of an N-(benzyloxycarbonyl)-ω-amino acid and ethylacarbonate corresponding to the general formula (III), wherein $R_4$ stands for ethoxycarbonyloxy and A stands for benzyloxycarbonylamino; and the obtained intermediate of the general formula (IV), wherein A' represents benzyloxycarbonylamino, is subjected to hydrogenolysis. Thus compounds of formula (I) are obtained, wherein R and $R_3$ each stand for hydrogen, and m is one.

The mixed anhydride of an N-(benzyloxycarbonyl)-ω-amino acid and ethylcarbonate, corresponding to the formula (III), is prepared by reacting a benzyloxycarbonyl-ω-amino acid with ethyl chloroformate. The obtained compound is preferably reacted with the starting substance of formula (II) directly in the reaction mixture, without isolation.

The invention is elucidated in detail by the aid of the following non-limiting examples.

EXAMPLE 1

1,4-Dihydro-1(4'-[chloroacetyl]-amino-phenyl)-3-(2H)-isoquinolinone 32.9 g. (0.138 moles) of 1-(4'-aminophenyl)-1,4-dihydro-3(2H)-isoquinolinone are dissolved in 250 ml. of glacial acetic acid at room temperature, with stirring. 15.2 g. (0.15 moles) of triethylamine, and subsequently 16.95 g. (0.15 moles) of chloroacetyl chloride are added slowly, dropwise to the clear solution. During the addition the temperature of the mixture raises generally to 40° to 45°C. After the addition the mixture is stirred at 50°C for 4 hours, then poured onto 2000 ml. of ice water. The separated precipitate is filtered off, washed well with water, dried, and recrystallized from butanol. 35.3 g. of the aimed product are obtained; m.p.: 241°–242°C.

Analysis: Calculated for $C_{17}H_{15}N_2O_2Cl$: C: 64.87 %, H: 4.80 %, N: 8.90 %, Cl: 11.26 %. Found: C: 64.82 %, H: 5.05 %, N: 8.99 %, Cl: 11.27 %.

EXAMPLE 2

1,4-Dihydro-1-(4'-chloroacetylamino-phenyl)-4,4-dimethyl-3(2H)-isoquinolinone 30.0 g. (0.1125 moles) of 1-(4'-aminophenyl)-1,4-dihydro-4,4-dimethyl-3(2H)-isoquinolinone are reacted in 280 ml. of glacial acetic acid with 14.7 g. (0.13 moles) of chloroacetyl chloride, in the presence of 13.5 g. (0.13 moles) of triethylamine. The reaction conditions are the same as described in Example 1. The crude product is recrystallized from ethanol to yield 25.15 g. of the title compound; m.p.: 218°–219°C.

Analysis: Calculated for $C_{19}H_{19}N_2O_2Cl$: C: 66.57 %, H: 5.59 %, N: 8.17 %, Cl: 10.34 %. Found: C: 66.46 %, H: 5.70 %, N: 8.39 %, Cl: 10.38 %.

EXAMPLE 3

1,4-Dihydro-1-(4'-chloroacetylamino-phenyl)-4-methyl-3(2H)-isoquinolinone 9.75 g. (0.0386 moles) of 1-(4'-aminophenyl)-1,4-dihydro-4-methyl-3(2H)-isoquinolinone are reacted, in 80 ml. of glacial acetic acid, with 5.64 g. (0.05 moles) of chloroacetyl chloride, in the presence of 5.06 g. (0.05 moles) of triethylamine. The reaction conditions are the same as described in Example 1. The crude product is recrystallized from butanol to yield 4.9 g. of the title compound; m.p. 238°–239°C.

Analysis: Calculated for $C_{18}H_{17}N_2O_2Cl$: C: 65.75 %, H: 5.21 %, N: 8.52 %, Cl: 10.78 %. Found: C: 65.78 %, H: 5.60 %, N: 8.74 %, Cl: 10.88 %.

EXAMPLE 4

1,4-Dihydro-4-isopropyl-1-(4'-chloroacetylamino-phenyl)-3(2H)-isoquinolinone 10.0 g. (0.0357 moles) of 1-(4'-aminophenyl)-1,4-dihydro-4-isopropyl-3(2H)-isoquinolinone are reacted, in 150 ml. of glacial acid, with 5.07 g. (0.045 moles) of chloroacetyl chloride in the presence of 4.55 g. (0.045 moles) of triethylamine. The reaction conditions are the same as given in Example 1. The crude product is recrystallized from butanol to yield 9.95 g. of the title compound; m.p.: 269°–270°C.

Analysis: Calculated for $C_{20}H_{21}N_2O_2Cl$: C: 67.31 %, H: 5.93 %, N: 7.85 %, Cl: 10.40 %. Found: C: 67.45 %, H: 6.20 %, N: 8.00 %, Cl: 10.05 %.

EXAMPLE 5

1,4-Dihydro-1-(4'-[propylaminoacetyl]-amino-phenyl)-3(2H)-isoquinolinone 7.4 g. (0.0236 moles) of 1,4-dihydro-1-(4'-chloroacetylamino-phenyl)-3(2H)-isoquinolinone are boiled in 200 ml. of propylamine for 12 hours. Thereafter 300 ml. of water are added to the mixture, and the propylamine is removed by distillation. The separated precipitate is filtered off, washed with water, dried and recrystallized from a mixture of acetone, and petroleum ether. 5.7 g. of the title compound are obtained; m.p.: 142°–144°C.

Analysis: Calculated for $C_{20}H_{23}N_3O_2$: C: 71.17 %, H: 6.87 %, N: 12.46 %. Found: C: 71.04 %, H: 7.19 %, N: 12.72 %.

EXAMPLE 6

1,4-Dihydro-4,4-dimethyl-1-(4'-[propylaminoacetyl]-amino-phenyl)3-(2H)-isoquinolinone 1.75 g. (0.0051 moles) of 1,4-dihydro-1-(4'-chloroacetylamino-phenyl)-4,4-dimethyl-3(2H)-isoquinolinone are reacted with 50 ml. of propylamine as described in Example 5. The crude product is recrystallized from a mixture of acetone and petroleum ether to yield 1.51 g. of the title compound; m.p.: 107°–108°C.

Analysis: Calculated for $C_{22}H_{27}N_3O_2$: C: 72.30 %, H: 7.45 %, N: 11.50 %. Found: C: 72.27 %, H: 7.59 %, N: 11.74 %.

EXAMPLE 7

1,4-Dihydro-4-methyl-1-(4'-[propylaminoacetyl]-aminophenyl)-3(2H)-isoquinolinone 11.9 g. (0.0362 moles) of 1,4-dihydro-1-(4'-chloroacetylamino-phenyl)-4-methyl-3(2H)-isoquinolinone are reacted with 50 ml. of propylamine. The reaction is carried out as described in Example 5, with the difference that the oily residue obtained after removing the propylamine is triturated with aqueous acetone. The crude product is recrystallized from a mixture of acetone and petroleum ether to yield 6.6 g. of the title compound; m.p.: 89-91°C.

Analysis: Calculated for $C_{21}H_{25}N_3O_2$: C: 71.78 %, H: 7.17 %, N: 11.96 %. Found: C: 71.60 %, H: 7.49 %, N: 12.06 %.

EXAMPLE 8

1,4-Dihydro-4-isopropyl-1-(4'-[propylaminoacetyl]-amino-phenyl)-3(2H)-isoquinolinone 9.95 g. (0.0279 moles) of 1,4-dihydro-4-isopropyl-1-(4'-chloroacetylamino-phenyl)3-(2H)-isoquinolinone are reacted with 75 ml. of propylamine. The reaction is carried out as described in Example 5, with the difference that the reaction mixture is poured onto 1500 ml. of ice water. The separated crude substance is recrystallized from ethyl acetate to yield 3.85 g. of the title compound; m.p.: 150-151 °C.

Analysis: Calculated for $C_{23}H_{29}N_3O_2$: C: 72.80 %, H: 7.70 %, N: 11.07 %. Found: C: 72.50 %, H: 7.74 %, N: 11.19 %.

EXAMPLE 9

1,4-Dihydro-1-(4'-[ethylaminoacetyl]-amino-phenyl)-3(2H)-isoquinolinone

A mixture of 9.43 g. (0.03 moles) of 1,4-dihydro-1-(4'-chloroacetylamino-phenyl)-3(2H)-isoquinolinone and 50 ml. of dry ethylamine is heated at 50°C in a sealed tube for 5 hours. The mixture is cooled and poured onto 200 ml. of ice water. The separated precipitate is filtered off, washed with water, dried under an IR lamp, and recrystallized from a mixture of acetone and petroleum ether. 7.1 g. of the title compound are obtained; m.p.: 183°–184°C.

Analysis: Calculated for $C_{19}H_{21}N_3O_2$: C: 70.56 %, H: 6.55 %, N: 13.00 %. Found: C: 70.64 %, H: 6.72 %, N: 13.29 %.

EXAMPLE 10

1,4-Dihydro-1-(4'-[ethylaminoacetyl]-amino-phenyl)-4,4-dimethyl-3(2H)-isoquinolinone 4.2 g. (0.01225 moles) of 1,4-dihydro-1-(4'-chloroacetylamino-phenyl)-4,4-dimethyl-3(2H)-isoquinolinone are reacted with dry ethylamine as described in Example 9, with the difference that heating is conducted for 6 hours at 70°C. The crude product is recrystallized from ethyl acetate to yield 3.24 g. of the title compound; m.p.: 151°–152°C.

Analysis: Calculated for $C_{21}H_{25}N_3O_2$: C: 71.78 %, H: 7.17 %, N: 11.96 %. Found: C: 71.73 %, H: 7.27 %, N: 12.12 %.

EXAMPLE 11

1,4-Dihydro-1-(4'-[methylaminoacetyl]-amino-phenyl)-3(2H)-isoquinolinone 9.44 g. (0.03 moles) of 1,4-dihydro-1-(4'-chloroacetylamino-phenyl)-3(2H)-isoquinolinone are reacted with 60 ml. of dry methylamine as described in Example 9, with the difference that heating is conducted for 6 hours at 50°C, and the reaction mixture is poured onto ice. The crude product is recrystallized from ethyl alcohol to yield 4.8 g. of the title compound; m.p.: 204°–205°C.

Analysis: Calculated C: 69.88 %, H: 6.19 %, N: 13.58 %. Found: C: 70.00 %, H: 6.08 %, N: 13.47 %.

EXAMPLE 12

1,4-Dihydro-1-(4'-[isopropylaminoacetyl]-amino-phenyl)-3(2H)-isoquinolinone 9.44 g. (0.03 moles) of 1,4-dihydro-1-(4'-chloroacetylamino-phenyl)-3(2H)-isoquinolinone are reacted with 70 ml. of dry isopropylamine as described in Example 10. The major part of the product separates from the reaction mixture. The mother liquor is poured onto water, and the isopropylamine is removed by distillation, to yield an additional crop of the product. The crude product is recrystallized from ethanol to yield 6.85 g. of the title compound; m.p.: 178°–179°C.

Analysis: Calculated for $C_{20}H_{23}N_3O_2$: C: 71.20 %, H: 6.87 %, N: 12.45 %. Found: C: 71.02 %, H: 7.18 %, N: 12.50 %.

EXAMPLE 13

1,4-Dihydro-4,4-dimethyl-1-(4'-[methylaminoacetyl]-amino-phenyl)-3(2H)-isoquinolinone maleate 5.15 g. (0.015 moles) of 1,4-dihydro-4,4-dimethyl-1-(4'-chloroacetylamino-phenyl)-3(2H)-isoquinolinone are reacted with 60 ml. of dry methylamine. The reaction is carried out as described in Example 9 with the difference, that heating is conducted for 7 hours at 60°C. The obtained 4.7 g. of crude product is reacted with maleic acid in ethanol. The salt is recrystallized from ethanol to yield 4.4 g. of the title compound; m.p.: 205°C (under decomposition). Analysis: Calculated for $C_{24}H_{27}N_3O_6$: C: 63.58 %, H: 6.00 %, N: 9.26 %. Found: C: 63.61 %, H: 6.23 %, N: 9.13 %.

EXAMPLE 14

1,4-Dihydro-4,4-dimethyl-1-(4'-[isopropylamino-acetyl]-amino-phenyl)-3(2H)-isoquinolinone 10.3 g. (0.03 moles) of 1,4-dihydro-4,4-dimethyl-1-(4'-chloroacetylamino-phenyl)-3(2H)-isoquinolinone are reacted with 70 ml. of isopropylamine as described in Example 9, with the difference that heating is conducted for 6 hours at 70° to 80°C. The crude product is recrystallized from ethanol to yield 4.15 g. of the title compound; m.p.: 132°–134°C Analysis: Calculated for $C_{22}H_{27}N_3O_2$: C: 72.30 %, H: 7.45 %, N: 11.50 %. Found: C: 72.54 %, H: 7.65 %, N: 11.52 %.

EXAMPLE 15

1,4-Dihydro-1-(4'-[butylaminoacetyl]-amino-phenyl)-4,4-dimethyl-3(2H)-isoquinolinone 10.3 g. (0.03 moles) of 1,4-dihydro-4,4-dimethyl-1-(4'-chloroacetylamino-phenyl)-3(2H)-isoquinolinone are reacted with 50 ml. of butylamine as described in Example 5, with the difference that the reaction mixture is boiled for 16 hours, and then, in order to separate the product, the mixture is poured onto 500 ml. of ice water. The crude product is recrystallized from ethanol to yield 5.1 g. of the title compound; m.p.: 133°–134°C.

Analysis: Calculated for $C_{23}H_{29}N_3O_2$: C: 72.80 %, H: 7.70 %, N: 11.07 %. Found: C: 72.99 %, H: 7.86 %, N: 11.26 %.

EXAMPLE 16

1,4-Dihydro-1-(4'-[N,N-diethylaminoacetyl]-amino-phenyl)-4,4-dimethyl-3(2H)-isoquinolinone 10.3 g. (0.03 moles) of 1,4-dihdyro-4,4-dimethyl-1-(4'-chloroacetylamino-phenyl)-3(2H)-isoquinolinone are reacted with 80 ml. of diethylamine as described in Example 5, with the difference that the reaction mixture is boiled for 14 hours and then, in order to separate the product, the mixture is poured onto 1000 ml. of water. The crude product is recrystallized from ethyl acetate to yield 8.0 g. of the title compound; m.p.: 174°–176°C.

Analysis: Calculated for $C_{23}H_{29}N_3O_2$: C: 72.79 %, H: 7.70 %, N: 11.08 %. Found: C: 72.54 %, H: 7.86 %, N: 11.24 %.

EXAMPLE 17

1,4-Dihydro-1-(4'-[ethylaminoacetyl]-amino-phenyl)-3(2H)-isoquinolinone maleate 0.6 g. (0.00186 moles) of 1,4-dihydro-1-(4'-/ethylaminoacetyl/-amino-phenyl)-3(2H)-isoquinolinone, prepared as described in Example 9, are reacted with 0.22 g. (0.0019 moles) of maleic acid in ethanol, under boiling. Upon cooling, 0.6 g. of the title compound separates from the reaction mixture; m.p.: 193-195°C (under decomposition).

Analysis: Calculated for $C_{23}H_{25}N_3O_6$: C: 62.85 %, H: 5.73 %, N: 9.56 %. Found: C: 62.87 %, H: 5.77 %, N: 9.83 %.

EXAMPLE 18

1,4-Dihydro-1-(4'-[benzyloxycarbonylamino-acetyl]-amino-phenyl)-4,4-dimethyl-3(2H)-isoquinolinone 3.72 g. (0.014 moles) of 1,4-dihydro-1-(4'-amino-phenyl)-4,4-dimethyl-3(2H)-isoquinolinone are dissolved in 30 ml. of dry dimethylformamide. The solution is cooled to 0°C, and 1.47 g. (0.0145 moles) of triethylamine are added with stirring. Thereafter a 0°C solution of 3.3 g. (0.0145 moles) of freshly prepared α-benzyloxycarbonylamino-acetylchloride in 20 ml. of dry dimethylformamide are added dropwise to the reaction mixture. The mixture is stirred at 0° to −5°C for 2 hours. During the reaction triehtylamine hydrochloride separates as a precipitate. The suspension is stirred at room temperature for 5 hours, thereafter poured onto 500 ml. of water. The separated oily substance is extracted with chloroform, the organic phase is washed with water, dried over sodium sulfate, and the solvent is removed by evaporation. The oily residue is triturated with water, the obtained solid substance is filtered off, washed well with water, and dried under an IR-lamp. The crude substance is recrystallized from ethanol to yield 1.4 g. of the title compound; m.p.: 210-211°C.

Analysis: Calculated for $C_{27}H_{27}N_3O_4$: C: 70.88 %, H: 5.95 %, N: 9.19 % Found: C: 71.01 %, H: 6.08 %, N, 8.96 %.

EXAMPLE 19

1,4-Dihydro-1-(4'-[benzyloxycarbonylamino-acetyl]-amino-phenyl)-4,4-dimethyl-3(2H)-isoquinolinone 5.23 g. (0.025 moles) of α-benzyloxycarbonylaminoacetic acid are dissolved in 50 ml. of dry dimethylformamide, and 2.53 g. (0.025 moles) of triethylamine are added to the stirred solution. The solution is cooled to −10°C, and 2.71 g. (0.025 moles) of ethyl chloroformate are added dropwise. The temperature rises to 0°C, and triethylamine hydrochloride separates in the form of a white precipitate. The mixture is stirred for 20 minutes, thereafter a 0°C solution of 6.65 g. (0.025 moles) of 1,4-dihydro-1-(4'-aminophenyl)-4,4-dimethyl-3(2H)-isoquinolinone in 50 ml. of dry dimethylformamide is added dropwise. After the addition the mixture is stirred at 0°C for 3 hours and at room temperature for 5 hours. The mixture is poured onto 1000 ml. of water, the separated substance is filtered off, washed well with water, and dried first in a vacuum desiccator over phosphorous pentoxide, and then under an IR-lamp. The crude product is recrystallized from ethanol to yield 6.0 g. of the title compound; m.p.: 211°-212°C.

Analysis: Calculated for $C_{27}H_{27}N_3O_4$: C: 70.88 %, H: 5.95 %, N: 9.19 %. Found: C: 70.50 %, H: 6.13 %, N: 9.08 %.

EXAMPLE 20

1,4-Dihydro-1-(4'-[aminoacetyl]-amino-phenyl)-4,4-dimethyl-3(2H)-isoquinolinone maleate 4.8 g. (0.0105 moles) of 1,4-dihydro-1-(4'-/benzyloxycarbonylamino-acetyl/-amino-phenyl)-4,4-dimethyl-3(2H)-isoquinolinone are dissolved in 150 ml. of dimethylformamide, and 0.72 g. (0.012 moles) of glacial acetic acid are added. Thereafter 2 g. of palladium catalyst are added to the mixture, and gaseous hydrogen is led over the solution until carbon dioxide evolution can be observed. When the evolution of carbon dioxide ceases, the catalyst is removed by filtration, the filtrate is evaporated to dryness, and the residue is taken up in water. The aqueous solution is rendered alkaline. An oily substance separates, which reapidly solidifies. The solid substance is filtered off, washed with water until neutral, and dried first in a vacuum desiccator over phosphorus pentoxide, and then under an IR-lamp. The obtained 2.3 g. of crude product is reacted with maleic acid in ethanol. 1.8 g. of the title compound are obtained; m.p.: 165°-167°C (under decomposition).

Analysis: Calculated for $C_{23}H_{25}N_3O_6$: C: 62.86 %, H: 5.73 %, N: 9.56 %. Found: C: 63.02 %, H: 5.90 %, N: 9.83 %.

What we claim is:
1. A compound of the formula

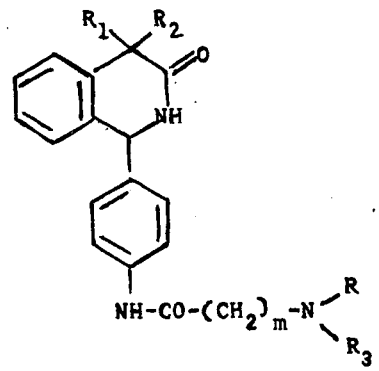

wherein
$R_1$ and $R_2$ each represent hydrogen or a straight-chained or branched $C_{1-3}$ alkyl group,
R stands for hydrogen or a straight-chained or branched $C_{1-4}$ alkyl group,
$R_3$ stands for hydrogen or a straight-chained or branched $C_{1-4}$ alkyl group and
R and $R_3$ may form together with the adjacent nitrogen atom pyrrolidino, piperidino or merphalino,
m is one,
or a pharmaceutically acceptable acid addition salt thereof.

2. A compound as claimed in claim 1, wherein $R_1$ and $R_2$ are the same and stand for hydrogen or methyl, R stands for hydrogen, $R_3$ stands for straight-chain or branched $C_{1-3}$ alkyl, and m is 1, or a pharmaceutically acceptable acid addition salt thereof.

3. 1,4-Dihydro-1-(4'-[ethylaminoacetyl]-amino-phenyl)-3(2H)-isoquinolinone.

* * * * *